(12) United States Patent
Schmitz

(10) Patent No.: US 6,168,634 B1
(45) Date of Patent: Jan. 2, 2001

(54) HYDRAULICALLY ENERGIZED MAGNETORHEOLOGICAL REPLICANT MUSCLE TISSUE AND A SYSTEM AND A METHOD FOR USING AND CONTROLLING SAME

(76) Inventor: Geoffrey W. Schmitz, 413 Lasalle St., Wausau, WI (US) 54403

(*) Notice: Under 35 U.S.C. 154(b), the term of this patent shall be extended for 0 days.

(21) Appl. No.: 09/275,953

(22) Filed: Mar. 25, 1999

(51) Int. Cl.[7] .................................................. A61F 2/54
(52) U.S. Cl. ............................................. 623/24; 414/4
(58) Field of Search .................... 623/24, 157; 901/2, 901/8, 9, 10, 22, 27, 28, 37; 335/29, 38; 414/2, 4

(56) References Cited

U.S. PATENT DOCUMENTS

| | | |
|---|---|---|
| 3,882,551 * | 5/1975 | Helmer et al. .................... 3/1 |
| 3,937,215 | 2/1976 | Bartholme . |
| 4,053,952 | 10/1977 | Goldstein . |
| 4,274,399 | 6/1981 | Mummert . |
| 4,369,814 | 1/1983 | Humphrey . |
| 4,379,335 | 4/1983 | Kirsch et al. . |
| 4,516,475 | 5/1985 | Fricke . |
| 4,536,893 | 8/1985 | Parravicini . |
| 4,615,260 | 10/1986 | TakBgi et al. . |
| 4,671,258 | 6/1987 | Bartholme . |
| 4,690,134 | 9/1987 | Snyders . |
| 4,720,087 | 1/1988 | Duclos et al. . |
| 4,733,758 | 3/1988 | Duclos et al. . |
| 4,739,692 | 4/1988 | WBssam et al. . |
| 4,772,407 | 9/1988 | Carlson . |
| 4,867,140 | 9/1989 | Hovis et al. . |
| 4,869,656 | 9/1989 | Della Sala . |
| 4,896,754 | 1/1990 | Carlson et al. . |
| 4,944,755 | 7/1990 | Hennequin et al. . |
| 4,957,477 | 9/1990 | Lundback . |
| 5,098,369 | 3/1992 | Heilman et al. . |
| 5,131,905 | 7/1992 | Grooters . |
| 5,269,811 * | 12/1993 | Hayes et al. ........................ 623/3 |
| 5,277,281 | 1/1994 | Carlson et al. . |
| 5,286,330 | 2/1994 | Carlson et al. . |
| 5,330,520 * | 7/1994 | Maddison et al. .................. 607/122 |
| 5,382,373 | 1/1995 | Carlson et al. . |
| 5,398,917 | 3/1995 | Carlson et al. . |
| 5,417,874 | 5/1995 | Carlson et al. . |
| 5,460,585 | 10/1995 | Gentry et al. . |
| 5,487,840 | 1/1996 | Yabe et al. . |
| 5,492,312 | 2/1996 | Carlson . |
| 5,501,581 | 3/1996 | Han . |
| 5,534,024 | 7/1996 | Rogers et al. . |
| 5,547,049 | 8/1996 | Weiss et al. . |
| 5,578,238 | 11/1996 | Weiss et al. . |
| 5,599,474 | 2/1997 | Weiss et al. . |
| 5,645,752 | 7/1997 | Weiss et al. . |
| 5,670,077 | 9/1997 | Carlson et al. . |
| 5,683,615 | 11/1997 | Munoz . |
| 5,713,954 | 2/1998 | Rosenberg et al. . |
| 5,951,600 * | 9/1999 | Lemelson ............................ 623/2 |
| 5,970,581 * | 10/1999 | Chadwick et al. .................. 16/421 |

FOREIGN PATENT DOCUMENTS

2054379 * 5/1980 (EP) ......................................... 623/24

* cited by examiner

*Primary Examiner*—David H. Willse
*Assistant Examiner*—Suzette J. Jackson
(74) *Attorney, Agent, or Firm*—Patents +TMS, P.C.

(57) ABSTRACT

A hydraulically energized magnetorheological replicant muscle tissue is provided as well as a system and method for using and controlling the same. The artificial muscle tissue is capable of causing motion, inducing force and enabling control thereof with life-like action. Numerous muscle tissue elements may be combined together to form a tissue capable of causing motion, inducing force and enabling control. Each muscle tissue element may receive fluid from a fluid supply. Control of fluid entering and exiting the muscle tissue element through valves may be effected using a central processing unit. As a result thereof, life-like action and artificial muscle tissue may be formed that replicates actual muscle tissue.

14 Claims, 4 Drawing Sheets

HYDRAULICALLY ENERGIZED MAGNETORHEOLOGICAL REPLICANT MUSCLE TISSUE AND A SYSTEM AND A METHOD FOR USING AND CONTROLLING SAME

BACKGROUND OF THE INVENTION

The present invention generally relates to artificial muscle tissue capable of causing motion, inducing force and enabling control thereof with life-like action and attributes for robotic, cybernetic and artificial prostheses. In addition, the present invention provides a system and a method for movement using artificial muscle tissue.

It is, of course, generally known to simulate human movements and provide animation to, for example, robots. However, it is difficult to replicate such "life-like" animation employing conventional methods such as by using electric motors, linear actuators, rotary actuators, hydraulic cylinders, pneumatic cylinders, linear electric motors, solenoids and other like devices.

Such conventional methods and devices do not exhibit the inherent flexibility necessary to simulate biological systems. This is particularly true in matters that require propulsion and motion where contemporary force actuators produce an unnatural action and/or response.

For example, in U.S. Pat. No. 4,053,952, a magnetic controlled valve, relief valve and pump enervated with magnetic fluid to close or contract passageways in the presence of magnetic flux are described. The valve controls the flow of a separate pressurized fluid but does not control the flow of pressurized magnetorheological fluid to an artificial muscle or organ.

In U.S. Pat. No. 4,923,057, the physical behavior of composite structures filled with electrorheological fluids are modified with changing electric fields. However, the invention does not teach the flow of materials into and out of composite structures or the addition of a pressurized operating fluid.

Other patents describe using bladders and reinforced bladders to generate pressure and motion, such as U.S. Pat. Nos. 4,274,399; 4,615,260; 4,739,692; 4,944,755; 4,957,477; 5,098,369; and 5,131,905. Motion may be induced across joints, and enervation of the heart, artificial hearts or other organs may be achieved. However, none of the devices employ magnetorheological or electrorheological working fluids.

A need, therefore, exists for a device, a system and a method designed to produce natural animal-like motion and response in machines to more realistically simulate action and attributes for control of robotic, cybernetic and artificial prostheses.

SUMMARY OF THE INVENTION

The present invention provides a lightweight, flexible, controlled artificial muscle tissue for robotics, cybernetics and artificial prostheses and other applications as well as a system and a method for achieving the same.

To this end, in an embodiment of the present invention, an artificial muscle tissue element is provided. The artificial muscle tissue element comprises a fiber forming an interior between a first end and a second end. A valve element is provided at each of the first end and the second end, or, two valves at a single end. Magnetorheological fluid is provided in the interior of the fiber wherein the fluid enters and exits through the valve elements.

In an embodiment, the valve elements include an electromagnetic coil.

In an embodiment, the fiber is linearly stiff and radially compliant.

In an embodiment, a plurality of fibers is provided wherein each of the plurality of fibers includes a valve element.

In an embodiment, the valve elements may be open, closed, or partially open.

In another embodiment of the present invention, an artificial muscle tissue is provided. The artificial muscle tissue comprises a plurality of muscle fiber elements each having an interior formed between a first end and a second end. Valve elements are associated with at least one end of each of the plurality of muscle fiber elements. Magnetorheological fluid in the interior of each of the plurality of fiber elements is provided wherein the fluid enters and exits through the valve elements.

In an embodiment, an anchor point is provided at one end of each of the plurality of fiber elements commonly connecting the ends.

In an embodiment, an electromagnetic coil is provided at an opening at one end of each of the plurality of fiber elements.

In an embodiment, each of the plurality of muscle fiber elements varies in size and number.

In another embodiment of the present invention, a system for replicating and controlling artificial muscle tissue is provided. The system has a plurality of muscle fiber elements connected commonly at their respective ends wherein each of the plurality of muscle fiber elements has an interior. Valve elements are associated with one end of each of the plurality of muscle fiber elements; magnetorheological fluid is provided in the interior of the fiber elements wherein the fluid enters and exits through the valve elements. Processing means is connected to each of the valve elements controlling the entry and egress of the magnetorheological fluid.

In an embodiment, heating means is connected to the processing means to control temperature of the fluid.

In an embodiment, an input means is connected to the processing means.

In an embodiment, a display means is connected to the processing means.

In an embodiment, the processing means controls variables associated with the fluid.

In another embodiment of the present invention, a method for replicating and controlling artificial muscle tissue is provided. The method comprises the steps of: providing a plurality of muscle fiber elements; circulating magnetorheological fluid through the plurality of muscle fiber elements; and controlling the circulation of the fluid through the plurality of muscle fiber elements.

In an embodiment, the temperature of the fluid to the plurality of muscle fiber elements is controlled.

In an embodiment, a valve is associated with each of the plurality of muscle fiber elements.

In an embodiment, the plurality of muscle fiber elements is connected in parallel between common anchor points.

In an embodiment, the plurality of muscle fiber elements is connected in parallel between common anchor points and in series with another plurality of muscle fiber elements.

In an embodiment, another plurality of muscle fiber elements is provided wherein a joint between the first plurality and the second plurality of muscle fiber elements is further provided.

It is, therefore, an advantage of the present invention to provide a lightweight, flexible, controlled artificial muscle tissue for robotics, cybernetics, and artificial prostheses as well as other applications.

Another advantage of the present invention is to form an artificial muscle tissue, system and method that operates in pairs where contraction in a muscle or muscles exhausts fluid from an opposing muscle and/or holds a position with equal forces applied across a joint and/or applies damping to joint motion.

And, another advantage of the present invention is to provide an artificial muscle tissue, system and method that operates singly where contraction in a muscle is opposed with a spring and/or pressure against the flexible walls of the container and/or gravity and/or other forces.

A further advantage of the present invention is to provide an artificial muscle tissue replacement for conventional techniques requiring electrical motors, linear actuators, rotary actuators, hydraulic cylinders, pneumatic cylinders, linear electric motors, solenoids, and/or other force/motion devices.

A still further advantage of the present invention is to provide a life-like means for powering and/or controlling robotic applications that outwardly resembles animal tissue in action, function, appearance and control.

And, another advantage of the present invention is to provide an artificial muscle element or elements that may be energized individually or in groups.

A further advantage of the present invention is to provide an artificial muscle element or elements where groups thereof may be energized in parallel and/or in series.

A still further advantage of the present invention is to provide an artificial muscle tissue that expands outwardly and that simultaneously shortens in length thereby contracting while simultaneously generating a force.

And, another advantage of the present invention is to provide an artificial muscle tissue, system and method that provides axial strength combined with torsional and bending flexibility.

Moreover, an advantage of the present invention is to provide an artificial muscle tissue, system and method that inherently limits maximum extension to prevent hyperextension and subsequent damage.

A further advantage of the present invention is to provide an artificial muscle tissue covered in an external sheath or covering to protect and/or hold together the same and/or provide turgor and/or retain lubricants and/or retain interstitial fillers and/or form a life-like appearance.

A still further advantage of the present invention is to provide an artificial muscle tissue coated and/or treated and/or surrounded with a lubricant or lubricants to reduce friction between muscle elements and/or layers and/or bundles and/or joints and/or connecting elements or the like.

And, another advantage of the present invention is to provide a muscle tissue system whose characteristics rely on the make-up of the individual muscle and joint element characteristics and geometry and the entire tissue or joint structure and geometry.

A further advantage of the present invention is to provide an artificial muscle tissue, system and method that is installed in layers and/or in multiple directions to produce desired motion and force characteristics. And, the muscle tissue may be organized with movable joints to generate vertical, pitch, roll, yaw, horizontal, as well as combinations of these and/or other motions.

A still further advantage of the present invention is to provide a hydraulically energized artificial muscle tissue, system and method that is energized with fluid pressure and flow.

And, another advantage of the present invention is to provide hydraulically energized artificial muscle tissue, system and method using magnetorheological and/or electrorheological fluids as a working medium.

A further advantage of the present invention is to provide muscle tissue elements, system and method that may be scaled in size, proportion and/or shape to generate desired force and/or motion characteristics.

Yet another advantage of the present invention is to provide an artificial muscle tissue, system and method that may be controlled with a valve or valve-like mechanisms to vary, halt, or permit fluid flow and/or pressure entering the muscle tissue or tissue elements.

A still further advantage of the present invention is to provide a system or method having valve control accomplished electronically using analog, digital or other controls to coordinate the muscle element and/or group function. Other controls, such as pneumatic and/or hydraulic and/or mechanical and/or photo and/or other controls may be applied independently or in combination with electronic control systems.

And, another advantage of the present invention is to provide artificial muscle elements and/or groups of elements that are multiple or single-ended having multiple or single openings for fluid exhaust and/or supply.

Further, an advantage of the present invention is to provide muscle element expansion or contraction due to elasticity of the muscle chamber which may be used as a hydraulic accumulator or reservoir.

And, yet another advantage of the present invention is to provide high strength and low stretch fibers that are incorporated within the expanding element housing or as a network external to the expanding element or elements.

A further advantage of the present invention is to provide an expanding element that may form a single piece containing the linear fibers in a wall or form a tube within a tube permitting the placement of either the outer casing or inner expanding element separately.

A still further advantage of the present invention is to provide an artificial muscle element or combinations of elements, filler material, lubricant, sheaths, connective tissue, control elements, movable joints and/or hydraulic tissues that may be combined to form artificial muscle/joint systems to generate desired motion or motions and force or forces.

Still further, another advantage of the present invention is to provide artificial muscle tissue where the operating fluid is optionally heated or cooled to permit low temperature and/or high temperature operation and/or to generate life-like sensible temperatures.

Moreover, an advantage of the present invention is to provide an artificial muscle tissue, system and method that forms a largely compliant structure that mimics animal tissue.

A further advantage of the present invention is to provide muscle force or forces that may vary through increased operating pressure.

Still further, an advantage of the present invention is to provide an artificial muscle element with characteristics that include, but are not limited to, volume, surface area, length, durometer, cross-section and shape.

And, yet another advantage of the present invention is to provide muscle velocity that is varied with fluid flow wherein the artificial muscle element characteristics include, but are not limited to, volume, surface area, length, durometer, cross-section and shape.

A still further advantage of the present invention is to provide a fluid optionally conveyed to the artificial muscle elements in parallel to reduce the effects of damaged elements and/or obtain desired control characteristics.

And, a further advantage of the present invention is to provide fluid optionally conveyed to the artificial muscle elements in series to multiply the elements' effects and/or obtain desired control characteristics.

Yet another advantage of the present invention is to provide interstitial spaces between artificial muscle elements, bundles, sheaths and other structures that may be optionally occupied with a filler material, such as silicone, silicone grease, foam or other materials, to form a life-like consistency and/or to act as a lubricant.

And, another advantage of the present invention is to provide an artificial muscle tissue, system and method capable of re-creating motions more typical of biological orgasms than conventional force generating elements.

A further advantage of the present invention is to provide motion or vibration of the artificial muscle tissue or combination of tissues, system and method which may be damped through controlling flow through orifices within the muscle hydraulic system.

A still further advantage of the present invention is to provide artificial muscle tissue that optionally forms a protective structure or sheath for internal organs or devices.

And, another advantage of the present invention is to provide an artificial muscle structure that provides a means for anchoring or fusing muscle tissue to itself, joints, connecting structures and/or other components.

Yet another advantage of the present invention is to provide an artificial muscle tissue, system and method that provides a means for conducting fluid to and/or from muscle elements.

A further advantage of the present invention is to provide an artificial muscle tissue, system and method that utilizes electromagnetic valves or orifices to control magnetic fluid passage through muscle elements with electronic based controls.

A still further advantage of the present invention is to provide artificial muscle elements and conductive tubing, as well as a system and method, that optionally contains pressure and/or fluid operated controls, such as check valves, to control fluid flow that does not require central or external valve activation but are dependent on fluid pressure and/or flow and/or flow direction and/or fluid temperature and/or fluid velocity and/or other parameters.

Yet another advantage of the present invention is to provide artificial muscle elements with physical characteristics, such as durometer of the expanding chamber material, that may be altered to change the muscle element response.

And, another advantage of the present invention is to provide artificial muscle elements wherein the physical characteristics and geometry of the linear, high strength-low stretch tensile fibers that may be altered to change the muscle element response, i.e. increased stretch to absorb energy at the end of muscle travel, that is additional hysteresis to protect the muscle element.

Moreover, an advantage of the present invention is to provide artificial muscle elements formed in various shapes to perform specialized tasks. For example, muscles may be ring-shaped, tissue elements along a length of a flexible-walled duct that may be arranged and coordinated to provide peristaltic motion similar to motion found in animal digestive tracts.

Yet another advantage of the present invention is to provide artificial muscle tissue where the "lay" of the reinforcing chord may be of alternate geometries to generate different responses to internal fluid pressure in the muscle element. Alternate lays include linear/crossing (at various angles), rectangular, as well as others.

A further advantage of the present invention is to provide an artificial hydraulic muscle tissue, system and method where the chambers may take alternate structures such as quilted, sheet-like, uniform cross-section, tapered and others.

A still further advantage of the present invention is to provide a basic artificial muscle element, system and method wherein artificial muscle elements may be organized independently, in connected segments or in continuous lengths.

And, a still further advantage of the present invention is to provide artificial muscle tissue that is compliant to permit close interaction with humans or fragile structures.

And, a still further advantage of the present invention is to provide an artificial muscle tissue, system and method that provides natural muscle organization, control and attachment in biological organisms that can be used as a guide for the placement, attachment and control of replicant muscle tissue.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention provides hydraulically actuated, flexible, lightweight artificial muscle tissues capable of causing motion, inducing force and enabling control with like-like action and attributes for robotic, cybernetic and artificial prostheses. In addition, the present invention provides a system and a method for simulating movement using artificial muscle tissue. To this end, a hybrid artificial muscle system combines numerous muscle elements together to form a tissue capable of causing motion, inducing force, and enabling control.

Figures 1, 2:
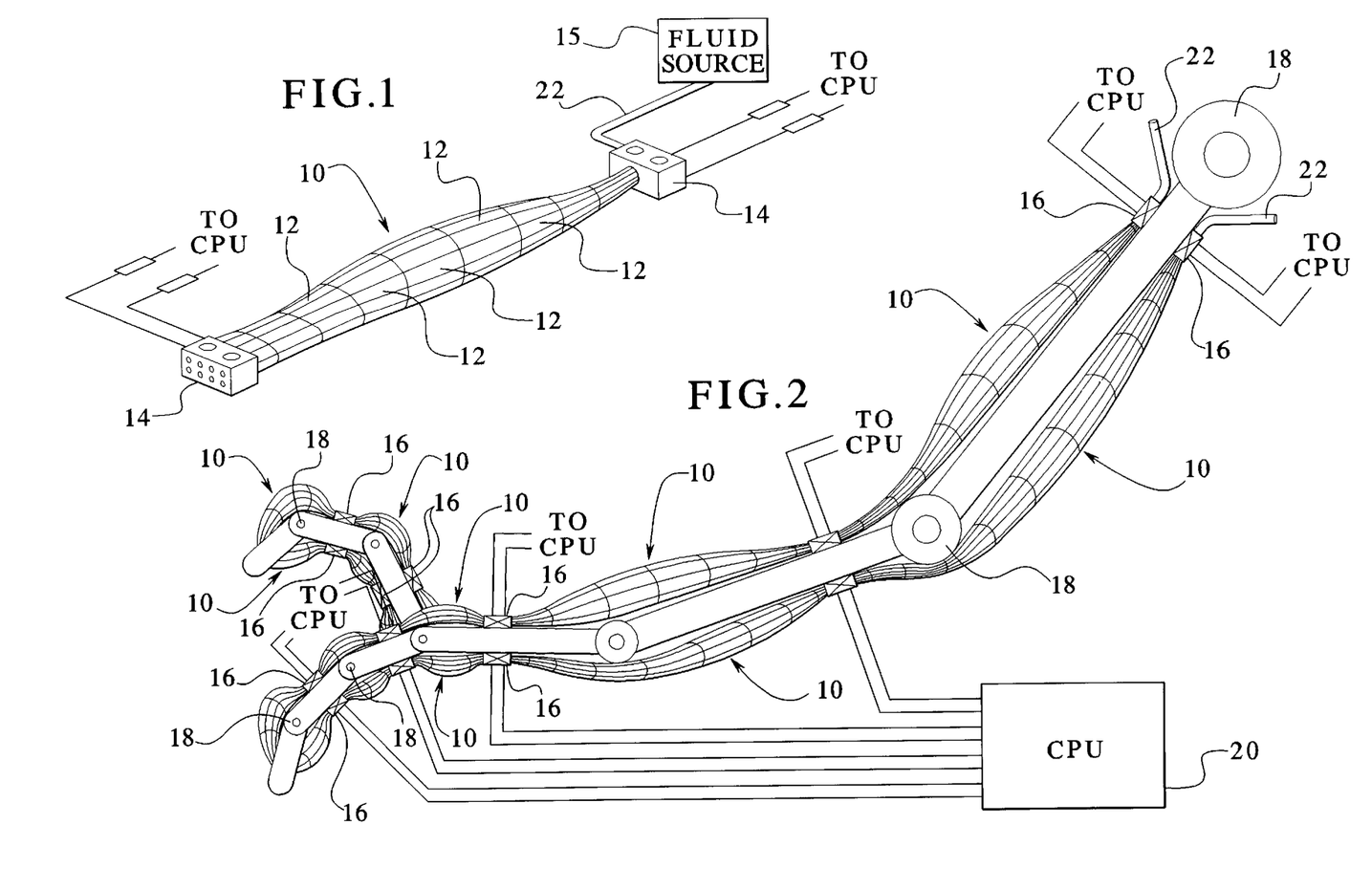
FIG. 1 illustrates a perspective view of a bundle of hydraulic fibers anchored between two points in an embodiment of the present invention.
FIG. 2 illustrates a side view of multiple bundles of hydraulic fibers interconnected between valve elements in another embodiment of the present invention.

Referring now to the drawings wherein like numerals refer to like parts, FIG. 1 generally illustrates a bundle 10 of hydraulic fibers or artificial muscle tissue elements 12 secured between anchor points 14. Each of the hydraulic fibers or elements 12 is formed from a linearly stiff and radially compliant chamber capable of receiving fluid under pressure from a fluid source 15. The bundle 10 may be wrapped in elastoplastic or elastomeric material, or the like, to simulate a look and feel of skin.

In a preferred embodiment, a magnetorheological fluid that is sensitive to magnetic fields is input from the fluid source 15 via an input 22 into the fibers or muscle tissue elements 12. Each of the elements 12 is fitted with a valve or valves 16 at each of the anchor points 14 that control fluid passing into and out of each of the element 12. Fluid control is achieved via a programmed central processing unit 20 (CPU). The CPU 20 may be suitably programmed by one skilled in the art to control fluid flow and/or pressure entering the muscle tissue elements 12.

In addition, heating or cooling of fluid may also be effected and controlled. This allows either low or high temperature operation and/or the potential to generate life-like temperatures. In addition, many other variables of the fluid may also be controlled through suitable programming of the CPU 20 including, but not limited to fluid pressure, fluid flow, flow direction, fluid temperature, fluid velocity, and/or combinations of any one or more of these variables. Of course, control of any combination of the fluid and/or the valves 16 associated with the elements 12 may be effected through suitable programming of the CPU 20.

Each of the anchor points 14 includes a servo or central valve 16 that controls the fluid passing into or out of each of the elements 12. Each of the elements 12 may contain single or multiple valves associated therewith or, alternatively, one central valve 16 may be associated with more than one of the elements 12. In a preferred embodiment, an orifice may be provided at an end of the elements 12 and may be equipped with an electromagnetic valve. The electromagnetic valve is simply an electromagnetic coil surrounding the orifice. When a magnetic field is applied or increased, particles within the working fluid align themselves along the lines of magnetic force restricting fluid entry or exit to the muscle tissue elements 12. The valves 16 may be closed, open or partially open or partially closed to act as a shut-off or a damping device, respectively.

When one valve is closed, for example, and fluid is forced into the chamber, the element 12 cannot expand in length and must expand in a radial direction. With radial expansion, the length of the element 12 decreases as the linear high-strength, low-stretch fibers of the muscle tissue elements 12 are forced away from the longitudinal axis. Decreasing length is accompanied with a linear force resulting from pressurized fluid expanding against a wall of the chamber 10. Accordingly, when fluid is forced into the muscle tissue element or elements 12 that are attached across a movable joint 18, motion results. The muscle tissue element or elements 12 may work together across the joint 18 with contraction of one muscle tissue element 12 exhausting fluid from an opposing muscle tissue element 12 and vice-versa. The muscle tissue element or elements 12 may be attached in numerous variations of size, number and direction to generate replicant behavior.

FIG. 2 shows an embodiment of the present invention illustrating various joints 18 connected between various lengths of the muscle tissue elements 12. The joints 18 are movable, and fluid may be forced into the muscle tissue elements 12 across the joint 18 resulting in motion. The muscle tissue elements 12 may work together across one or more of the joints 18 with the contraction with one of the muscle tissue elements 12 exhausting fluid from an opposing one of the muscle tissue elements 12 and vice versa as previously set forth. The muscle tissue elements 12 are attached between the joints 18 and may also be independently controlled between the joints 18.

To this end, the CPU 20 may be programmed to control each of the valves 16 at the anchor points 14 between the joints 18. The CPU 20 is implemented to control timing and application of pressure, valve opening and closing, damping application, monitoring of joint position, acceleration, and other parameters to coordinate joint motion within a single joint and orchestrate multiple ones of the muscle tissue elements 12 and the joints 18 together. Accordingly, any movement may be simulated between the joints 18.

For example, as illustrated in FIG. 2, an arm and fingers may be simulated showing all of the joints 18, such as (from right to left in FIG. 2) a shoulder, an elbow, a wrist and knuckles of the fingers. Each of the movements between the joints 18 may be simulated to replicate life-like action. The input 22 from the fluid source 15 is associated with at least one of the valves 16 at the anchor element 14. As a result, the fundamental muscle tissue element 12 forms the linearly stiff and radially compliant chamber capable of receiving fluid, either magnetorheological (magnetic) and/or electrorheological fluid. Fluid may be received under pressure individually or in groups fitted with electromagnetic valves to control fluid flow. Fluid is forced into the chamber 10 via the elements 12 to radially expand thereby increasing the length of the muscle tissue element 12 with an accompanying linear force and turgor. As a result, useful motion from fluid forced into the muscle tissue element or elements 12 may be achieved.

The movable joints 18 may work in pairs with one contraction exhausting fluid from opposing muscle tissue elements 12 that hold a position of equivalent forces or damping or as single elements operating against gravitational, spring, elastomer contraction or other forces. Magnetorheological and/or electrorheological fluid and valves may be employed for proportional flow and damping control without conventional mechanical valve elements. Placed singly, in bundles, rings or layers, in similar or differing directions, isolated or inside sheaths optionally filled with filler or lubricant supplied with fluid in parallel or in series, the elements 12 and the joints 18 combine to form a working muscle/joint system to mimic biological structures. The CPU 20 may be suitably programmed to control the fluid pressure timing, valve application damping within a single joint and/or orchestrates multiple muscle elements/joints together.

Figures 3, 4:
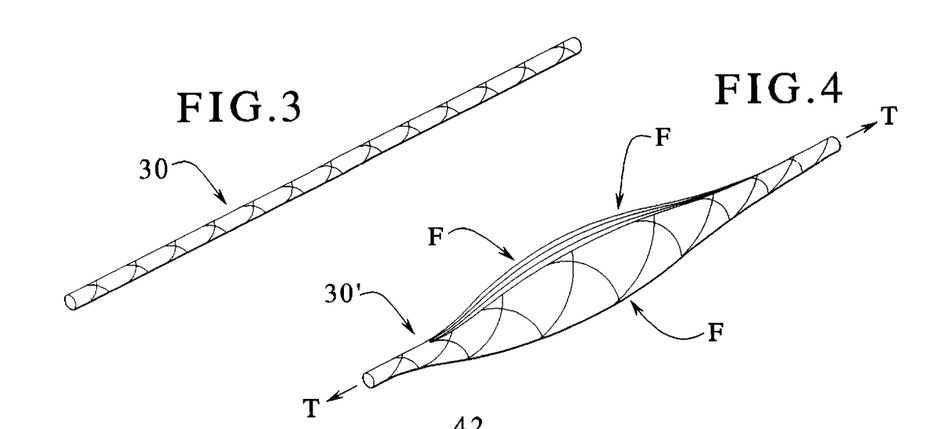
FIG. 3 illustrates a perspective view of a relaxed fiber in an embodiment of the present invention.
FIG. 4 illustrates a perspective view of a pressurized fiber in an embodiment of the present invention.

FIGS. 3–6 illustrate various embodiments of muscle elements. FIG. 3 illustrates an elastic tube 30 having relaxed fibers. FIG. 4 illustrates a pressurized fiber 30' that results from varying forces F and turgor T applied from fluid controlled through the fibers 30'.

Figures 5, 6:
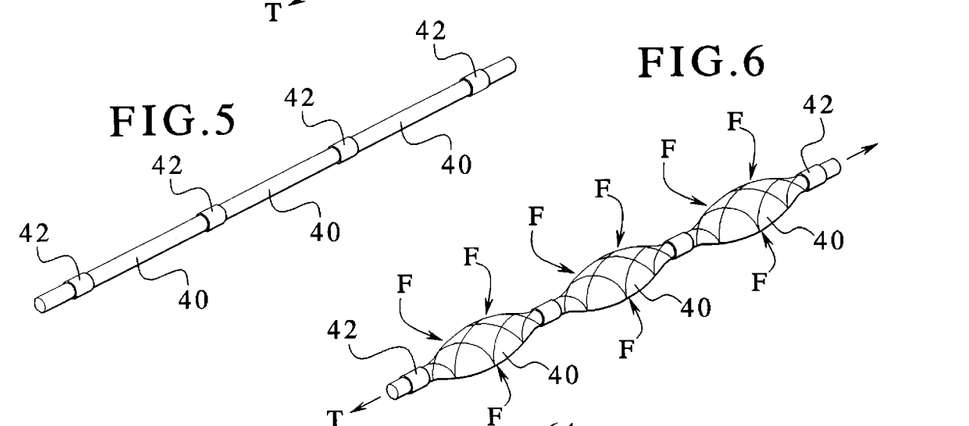
FIG. 5 illustrates a perspective view of a multi-segmented relaxed fiber in an embodiment of the present invention.
FIG. 6 illustrates a perspective view of a multi-segmented pressurized fiber in an embodiment of the present invention.

FIGS. 5 and 6 illustrate fibers 40 between connecting elements 42. Each of the connecting elements 42 may include a valve for control of fluid to each of the fibers 40. Accordingly, varying forces F and turgor T may be applied to effectuate each of the fibers 40 individually or in combination as shown in FIG. 6.

Figure 7:
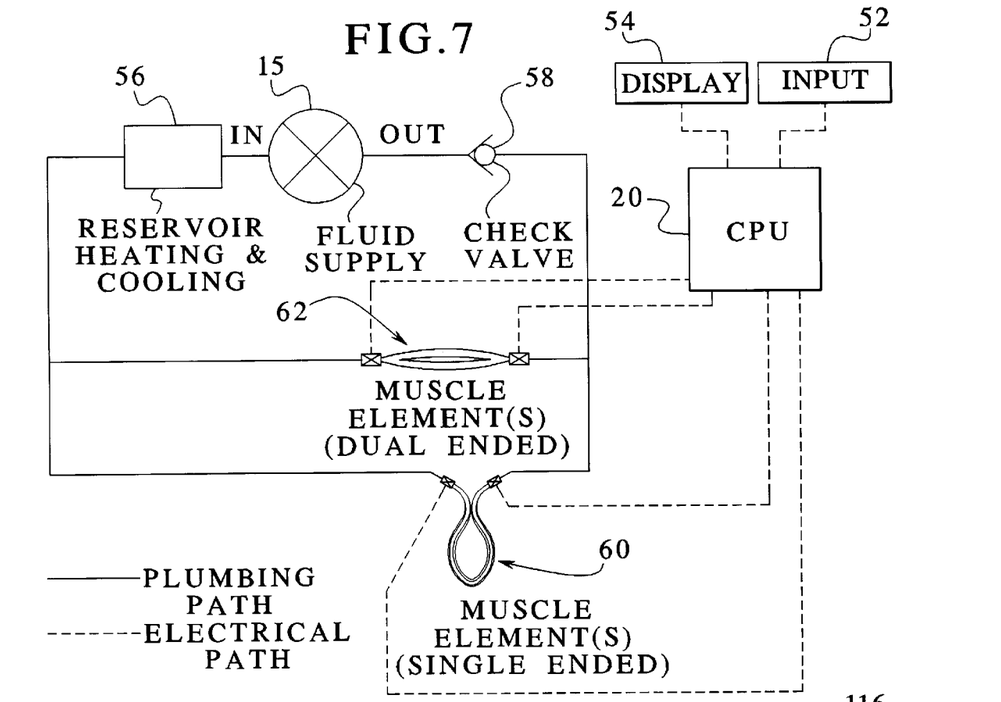
FIG. 7 illustrates a black box/schematic diagram of the functional components of an embodiment of the system of the present invention.

FIG. 7 generally illustrates a black box diagram of the components of a system 50 necessary for effecting control and delivery of fluid to the muscle elements shown and previously described with reference to FIGS. 1–6. Namely, a fluid supply 15 of magnetorheological fluid is provided. The fluid supply 15 may be heated or cooled to a desired temperature by a heating and cooling means 56 as may be programmed and controlled by the CPU 20. An input device 52 may be provided to alter the programming of the CPU 20 and to effect immediate changes to the circulation of fluid in the system 50. And, a display 54 may be provided to provide real time information regarding the operation of the system 50. As a result, an individual may effect operation of the system 50 based on data presented on the display 54 and may effect changes via the input device 52. The input device 52 may also be used to re-program the CPU 20 as may be necessary and may be implemented by one of ordinary skill in the art.

As shown in FIG. 7, the dashed lines indicate electrical connections or paths between various components of the system 50, and the solid lines indicate fluid or plumbing baths between components of the system 50. A check valve 58 may also be provided as generally shown in FIG. 7. Both a single-ended muscle element 60 and a dual-ended muscle element 62 is shown in FIG. 7 for illustration purposes. Of course, many combinations of any type of muscle elements may be implemented by one of ordinary skill in the art.

Figures 8, 11:
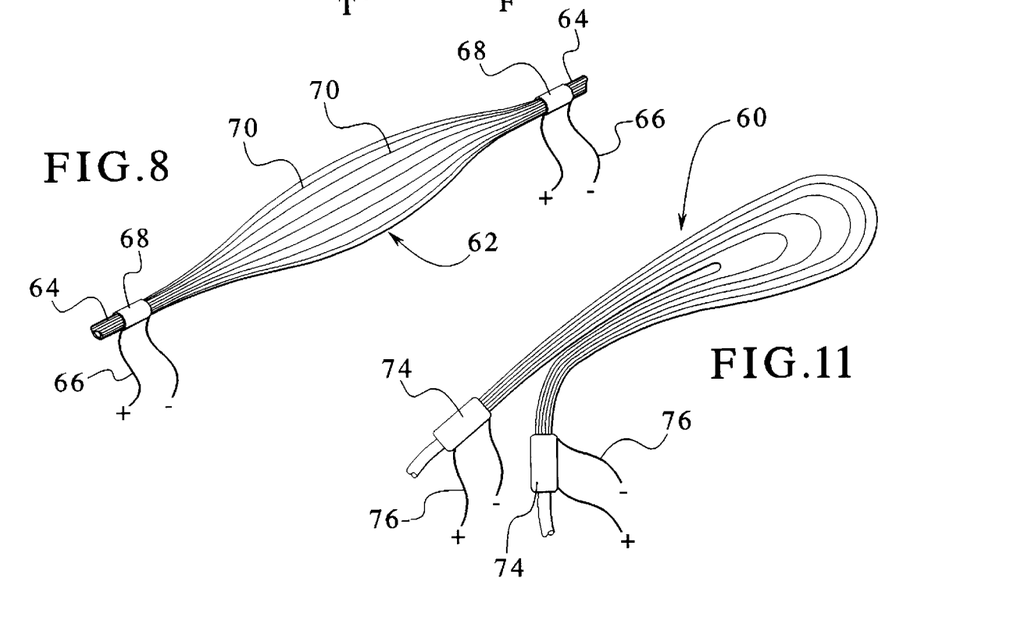
FIG. 8 illustrates a perspective view of a dual ended muscle element in an embodiment of the present invention.
FIG. 11 illustrates a perspective view of an embodiment of a single ended muscle element of the present invention.
Figure 9:
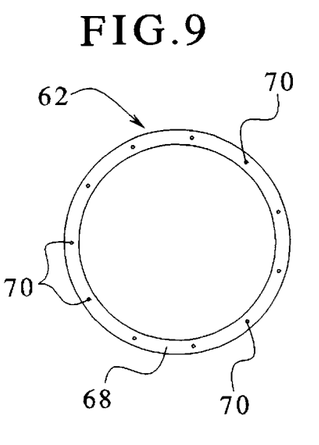
FIG. 9 illustrates a cross-sectional view of an embodiment of a valve with cords of the muscle element extending therethrough.
Figure 10:
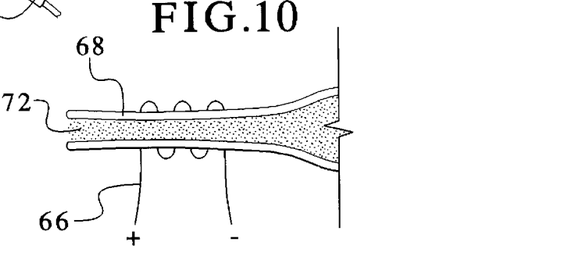
FIG. 10 illustrates a cross-sectional view of an embodiment of a coil of the present invention surrounding a valve.

FIG. 8 generally illustrates the dual muscle element 62 wherein each end 64 of the muscle element 62 has an orifice surrounded by an electromagnetic coil 66 associated with valves 68. As shown in the enlarged cross-sectional view in FIG. 8, stiff linear cords 70 of the muscle element 62 extend through the tube that defines the valve 68. A cross-section of the valve 68 is shown in FIG. 10 with the coil 66 surrounding the valve 68. Fluid 72 is shown flowing through the valve 68.

FIG. 11 generally illustrates the single-ended muscle element 60 that preferably includes two valves 74 with coils 76 surrounding the orifices of the valves 74. The valves 74 may be programmed to control flow of fluid into a low pressure return manifold.

Figure 12:
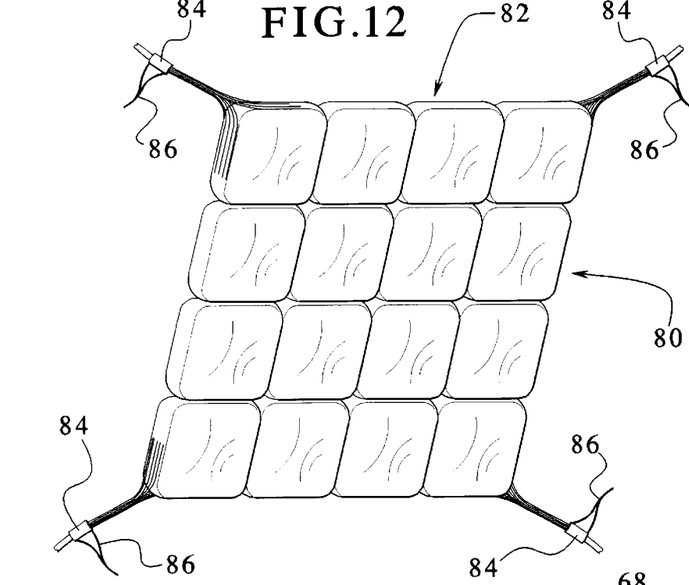
FIG. 12 illustrates a perspective view of an embodiment of a muscle element of the present invention arranged as a quilted sheet.
Figure 13:
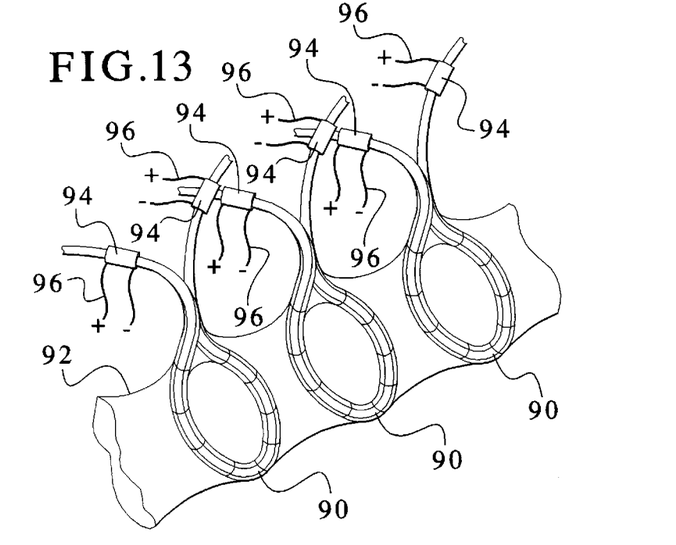
FIG. 13 illustrates a perspective view of an embodiment of muscle elements of the present invention organized as toroids integral with a flexible tube capable of generating peristaltic motion.

FIGS. 12 and 13 generally illustrate alternate embodiments of muscle tissue elements. FIG. 12 illustrates a quilted sheet 80 of muscle tissue elements 82. Valves 84 may be located at respective orifices at corners of the quilted sheet 80 as generally shown in FIG. 12 with coils 86 surrounding the orifices of the valves 84.

FIG. 13 illustrates muscle elements 90 arranged as toroids integral within a flexible tube 92 to generate peristaltic motion. Each of the muscle elements 90 is single-ended and includes valves 94 arranged at orifices of the muscle elements 90. Coils 96 are associated with each of the orifices of the valves 94.

Figure 14:
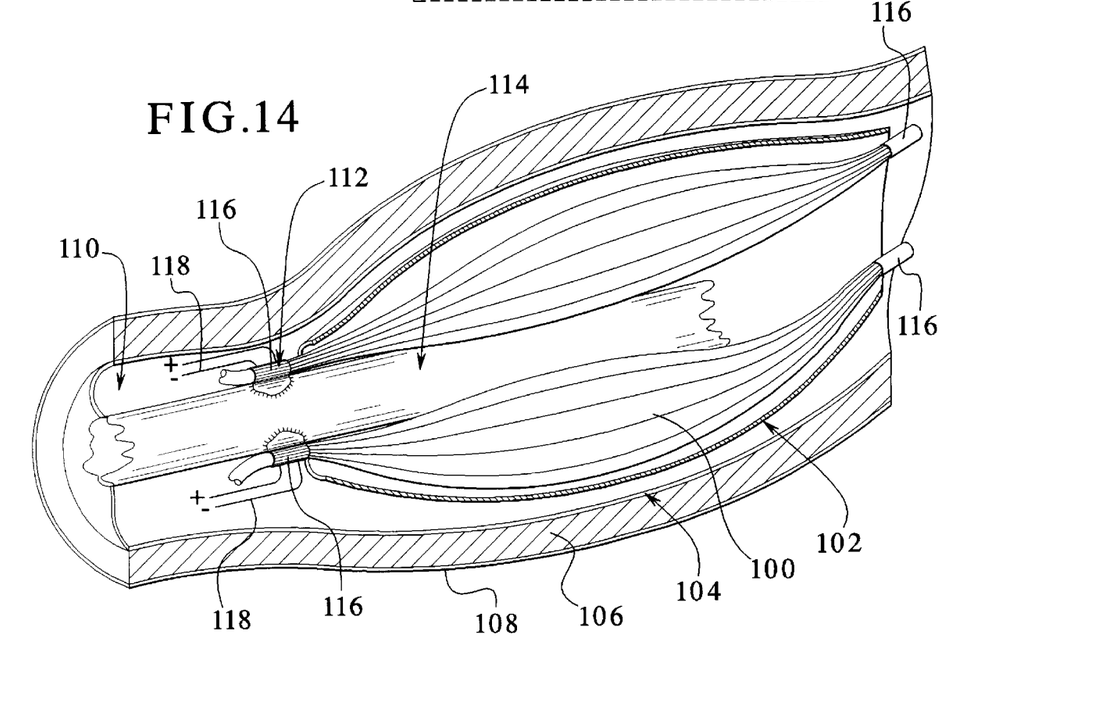
FIG. 14 illustrates a partially broken-away, partially cross-sectional and perspective view of tissue organization for incorporating with an embodiment of a muscle element of the present invention.

Finally, referring now to FIG. 14, a cross-sectional view of tissue organization surrounding a muscle element 100 is generally shown. Around the muscle element 100 is a contractible sheet 102. A low friction sheet 104 may further be provided as a layer on an interior side of an exterior layer that includes an energy absorbing fatty layer 106 as an intermediate layer and a tough, contractile outer skin 108 as an outer layer. Between the contractile sheet 102 and the low friction sheet 104 may be provided interstitial space 110 which may be filled with lubricant or other material. A skeletal anchor 112 is generally shown for attaching the muscle element 100 to the skeletal member 114. The remaining elements, such as valves 116 and coils 118, are generally shown and elements, such as illustrated in FIG. 14 and may be implemented and attached to the system in a known manner by those skilled in the art.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

I claim:

1. An artificial muscle tissue element comprising:
   a fiber forming an interior between a first end and a second end;
   a valve element at each of the first end and the second end; and
   magnetorheological fluid in the interior of the fiber wherein the fluid enters and exits through the valve elements.

2. The element of claim 1 wherein the valve elements include an electromagnetic coil.

3. The element of claim 1 wherein the fiber is linearly stiff and radially compliant.

4. The element of claim 1 further comprising:
   a plurality of fibers wherein each of the plurality of fibers includes a valve element.

5. The element of claim 1 wherein the valve elements may be open, closed, or partially open.

6. An artificial muscle tissue comprising:
   a plurality of muscle fiber elements each having an interior formed between a first end and a second end;
   valve elements associated with at least one end of each of the plurality of muscle fiber elements; and
   magnetorheological fluid in the interior of each of the plurality of fiber elements wherein the fluid enters and exits through the valve elements.

7. The tissue of claim 6 further comprising:
   an anchor point at one end of each of the plurality of fiber elements commonly connecting the ends.

8. The tissue of claim 6 further comprising:
   an electromagnetic coil at an opening at one end of each of the plurality of fiber elements.

9. The tissue of claim 6 wherein each of the plurality of muscle fiber elements varies in size and number.

10. A system for replicating and controlling artificial muscle tissue, the system comprising:

a plurality of muscle fiber elements connected commonly at their respective ends wherein each of the plurality of muscle fiber elements has an interior;

valve elements associated with one end of each of the plurality of muscle fiber elements;

magnetorheological fluid in the interior of the fiber elements wherein the fluid enters and exits through the valve elements; and processing means connected to each of the valve elements controlling the entry and egress of the magnetorheological fluid.

11. The system of claim 10 further comprising:

heating means connected to the processing means to control temperature of the fluid.

12. The system of claim 10 further comprising:

input means connected to the processing means.

13. The system of claim 10 further comprising:

display means connected to the processing means.

14. The system of claim 10 wherein the processing means controls variables associated with the fluid.

* * * * *